(12) United States Patent
Usuda

(10) Patent No.: US 12,232,690 B2
(45) Date of Patent: Feb. 25, 2025

(54) ENDOSCOPE SYSTEM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 512 days.

(21) Appl. No.: 17/167,046

(22) Filed: Feb. 3, 2021

(65) Prior Publication Data

US 2021/0177248 A1 Jun. 17, 2021

Related U.S. Application Data

(63) Continuation of application No. PCT/JP2019/032166, filed on Aug. 16, 2019.

(30) Foreign Application Priority Data

Aug. 17, 2018 (JP) .................. 2018-153733

(51) Int. Cl.
| | | |
|---|---|---|
| *A61B 1/00* | (2006.01) | |
| *A61B 1/018* | (2006.01) | |
| *A61B 1/06* | (2006.01) | |
| *G06V 10/25* | (2022.01) | |
| *G06V 10/764* | (2022.01) | |

(52) U.S. Cl.
CPC ........ *A61B 1/000094* (2022.02); *A61B 1/018* (2013.01); *A61B 1/0655* (2022.02); *G06V 10/25* (2022.01); *G06V 10/764* (2022.01)

(58) Field of Classification Search
CPC . A61B 1/000094; A61B 1/018; A61B 1/0655; G06V 10/25; G06T 2207/30096; G02B 23/2484

See application file for complete search history.

(56) References Cited

U.S. PATENT DOCUMENTS

| | | |
|---|---|---|
| 8,497,898 B2 | 7/2013 | Moriyama et al. |
| 8,768,024 B1 | 7/2014 | Zingman et al. |
| 10,863,893 B2 | 12/2020 | Imaizumi et al. |

(Continued)

FOREIGN PATENT DOCUMENTS

| | | |
|---|---|---|
| CN | 102834043 | 12/2012 |
| CN | 107708521 | 2/2018 |

(Continued)

OTHER PUBLICATIONS

"Search Report of Europe Counterpart Application", issued on Sep. 6, 2021, p. 1-p. 7.

(Continued)

*Primary Examiner* — John P Leubecker
*Assistant Examiner* — Li-Ting Song
(74) *Attorney, Agent, or Firm* — JCIPRNET

(57) ABSTRACT

An endoscope system includes an image obtaining unit that obtains an image obtained by image capturing of a photographic subject, a recognition unit that performs a recognition process of recognizing the photographic subject by using the image, an identification unit that identifies an operation performed on the photographic subject, a setting unit that enables or disables the recognition unit in accordance with the result of identification by the identification unit, and a notification unit that gives a notification of whether the recognition unit is enabled or disabled.

19 Claims, 10 Drawing Sheets

(56) References Cited

U.S. PATENT DOCUMENTS

| | | | |
|---|---|---|---|
| 11,025,835 B2 | 6/2021 | Kuriyama et al. | |
| 11,145,053 B2 | 10/2021 | Hayami et al. | |
| 11,170,498 B2 | 11/2021 | Kono et al. | |
| 2005/0049458 A1 | 3/2005 | Honda et al. | |
| 2010/0004505 A1 | 1/2010 | Umemoto et al. | |
| 2011/0301443 A1 | 12/2011 | Yamaguchi et al. | |
| 2013/0188029 A1 | 7/2013 | Takahashi | |
| 2014/0371527 A1* | 12/2014 | Sato | A61B 1/000094 600/106 |
| 2018/0092700 A1* | 4/2018 | Itkowitz | A61B 90/36 |
| 2018/0098690 A1 | 4/2018 | Iwaki | |
| 2018/0114319 A1* | 4/2018 | Kono | A61B 1/018 |
| 2018/0249900 A1* | 9/2018 | Imaizumi | G02B 23/2484 |
| 2019/0130565 A1* | 5/2019 | Lee | G06N 3/08 |
| 2019/0311476 A1* | 10/2019 | Hayami | A61B 5/7264 |
| 2020/0090333 A1 | 3/2020 | Iwaki | |
| 2022/0151462 A1* | 5/2022 | Usuda | G16H 50/20 |
| 2023/0050945 A1* | 2/2023 | Nakaue | G06T 7/0012 |
| 2024/0312019 A1* | 9/2024 | Higa | A61B 6/12 |

FOREIGN PATENT DOCUMENTS

| | | |
|---|---|---|
| EP | 3633987 | 4/2020 |
| JP | S63259614 | 10/1988 |
| JP | H03277340 | 12/1991 |
| JP | 2005073799 | 3/2005 |
| JP | 2007330405 | 12/2007 |
| JP | 2008245840 | 10/2008 |
| JP | 2011254936 | 12/2011 |
| JP | 2013150658 | 8/2013 |
| JP | 2015096237 | 5/2015 |
| JP | 2018051364 | 4/2018 |
| WO | 2016199273 | 12/2016 |
| WO | 2017072853 | 5/2017 |
| WO | 2017081976 | 5/2017 |
| WO | 2018105063 | 6/2018 |
| WO | 2018216188 | 11/2018 |

OTHER PUBLICATIONS

"International Search Report (Form PCT/ISA/210) of PCT/JP2019/032166," mailed on Oct. 29, 2019, with English translation thereof, pp. 1-5.

"Written Opinion of the International Searching Authority (Form PCT/ISA/237) of PCT/JP2019/032166," mailed on Oct. 29, 2019,, with English translation thereof, pp. 1-9.

"Office Action of Japan Counterpart Application", issued on Aug. 29, 2023, with English translation thereof, p. 1-p. 6.

"Office Action of China Counterpart Application", issued on Nov. 22, 2023, with English translation thereof, p. 1- p. 17.

"Office Action of Europe Counterpart Application", issued on Mar. 13, 2024, p. 1-p. 6.

* cited by examiner

|  | DETECTION | DETERMINATION |
|---|---|---|
| IDENTIFICATION STATE 1 | ON | ON |
| IDENTIFICATION STATE 2 | ON | OFF |
| IDENTIFICATION STATE 3 | OFF | ON |
| IDENTIFICATION STATE 4 | OFF | OFF |

ENDOSCOPE SYSTEM

CROSS-REFERENCE TO RELATED APPLICATIONS

This application is a Continuation of PCT International Application No. PCT/JP2019/032166 filed on 16 Aug. 2019, which claims priority under 35 U.S.C § 119(a) to Japanese Patent Application No. 2018-153733 filed on 17 Aug. 2018. The above application is hereby expressly incorporated by reference, in its entirety, into the present application.

BACKGROUND OF THE INVENTION

1. Field of the Invention

The present invention relates to an endoscope system that performs a recognition process for a photographic subject using an image captured by using an endoscope.

2. Description of the Related Art

In the medical field, endoscope systems that include a light source device, an endoscope, and a processor device are in widespread use. The light source device generates illumination light. The endoscope captures an image of a photographic subject by using an image sensor. The processor device generates an image and performs other image processing and so on.

Endoscope systems may not only capture an image of a photographic subject for observation but also have additional functions. For example, an endoscope system that has an "input mode" in which the position and orientation of a treatment tool are controlled by using a touch panel is known (JP2008-245840A (corresponding to US2010/0004505A1)). In the endoscope system described in JP2008-245840A, the state of the input mode is displayed on a screen. An endoscope system that has a function of displaying on a screen an image representing the bending state of a tip part of an endoscope and a character string for notification of, for example, completion of calibration to thereby give a notification of, for example, a system error is known (JP2007-330405A). In addition, an endoscope system that displays on a screen the ON state or the OFF state of a foot switch (JP2005-073799A (corresponding to US2005/0049458A1)), an endoscope system that displays on a screen a mark indicating that air supply is ongoing (JP991-277340A (JP-H03-277340A)), and an endoscope system that displays on a screen the ON state or the OFF state of image recording (JP1988-259614A (JP-S63-259614A)) are known.

Further, endoscope systems that detect a treatment tool and use the result of detection are known. For example, an endoscope system that uses the result of detecting a treatment tool to determine the correction intensity of an image is known (JP2015-96237A). An endoscope system that inactivates an autofocus function in a case where a treatment tool is detected is known (JP2013-150658A (corresponding to US2013/0188029A1)).

In addition, currently, an endoscope system that supports diagnoses by, for example, calculating biological function information using a captured image of a photographic subject is known (JP2018-51364A).

SUMMARY OF THE INVENTION

In a case where a medical image, such as an image captured by using an endoscope (hereinafter referred to as an endoscopic image), is used to recognize a photographic subject having specific characteristics or part of the photographic subject, thereby obtaining information for supporting a diagnosis (hereinafter referred to as diagnosis support information), it is necessary to use a medical image that is captured under specific conditions such that a recognition process can function for the medical image. When a medical image for which a recognition process does not function is used, even when the result of the recognition process is obtained, the result of the recognition process may be inaccurate.

It is not necessarily the case that a medical image for which a recognition process can function is always obtained. Accordingly, an inaccurate result of the recognition process or diagnosis support information obtained by, for example, calculation using an inaccurate result of the recognition process may hinder observation or a diagnosis of the photographic subject. For example, in endoscope systems, the accuracy of a recognition process may decrease in a case where a treatment tool is present in an endoscopic image.

In order not to provide, for example, an inaccurate result of a recognition process as described above, the recognition process can be prevented from being performed unless a medical image for which the recognition process can function is obtained. However, when the recognition process is simply prohibited from being performed, a doctor or the like, who is a user, may incorrectly recognize the result of performing the recognition process or the result of not performing the recognition process. For example, in a case of using, for example, an apparatus that performs a recognition process for detecting a potential lesion, when the recognition process is simply prohibited from being performed, a doctor or the like who is using the apparatus may incorrectly recognize that the recognition process is performed and a potential lesion is not detected as a result of the recognition process. That is, a doctor or the like may unable to determine whether the result of the recognition process is not displayed because the recognition process is not performed or the result of the recognition process is not displayed because the recognition process is performed and a recognition target is not detected as a result of the recognition process.

For example, in a case where a doctor or the like starts, for example, a surgical operation on a photographic subject or in a case where a doctor or the like sprays a coloring agent and starts close observation, a recognition process or display of the result of the recognition process may be automatically disabled in order not to hinder an operation of the doctor or the like. Also in this case, the doctor or the like may incorrectly recognize the result of performing the recognition process or the result of not performing the recognition process as in the above-described case. In addition, in a case where a recognition function is automatically disabled although a doctor or the like does not explicitly disable the recognition function, the doctor or the like may lose concentration, which is a problem.

An object of the present invention is to provide an endoscope system that at least prevents incorrect recognition of the result of performing a recognition process and the result of not performing the recognition process.

An endoscope system according to the present invention includes: an image obtaining unit that obtains an image obtained by image capturing of a photographic subject; a recognition unit that performs a recognition process of recognizing the photographic subject by using the image; an identification unit that identifies an operation performed on the photographic subject; a setting unit that enables or disables the recognition unit in accordance with a result of identification by the identification unit; and a notification unit that gives a notification of whether the recognition unit is enabled or disabled.

Preferably, the identification unit determines whether or not an operation is performed on the photographic subject.

Preferably, the identification unit identifies a type of the operation performed on the photographic subject.

Preferably, the operation identified by the identification unit is use of a treatment tool.

Preferably, the operation identified by the identification unit is spraying of a liquid on the photographic subject.

Preferably, the setting unit disables the recognition unit in a case where an operation is performed on the photographic subject, and enables the recognition unit in a case where no operation is performed on the photographic subject.

Preferably, the setting unit disables the recognition unit in a case where a specific operation is performed on the photographic subject.

Preferably, the setting unit enables or disables the recognition process that is performed by the recognition unit.

Preferably, the setting unit enables or disables giving of a notification of a result of the recognition process.

Preferably, the notification unit gives a notification of the result of identification by the identification unit in addition to whether the recognition unit is enabled or disabled.

Preferably, the recognition unit recognizes presence or absence of a lesion or a potential lesion of the photographic subject or recognizes a type or a degree of progression of a lesion or a potential lesion of the photographic subject.

Preferably, in a case where the recognition unit performs a plurality of types of recognition processes, the setting unit enables or disables each of the recognition processes.

According to the present invention, it is possible to provide an endoscope system that prevents incorrect recognition of the result of performing a recognition process and the result of not performing the recognition process.

DESCRIPTION OF THE PREFERRED EMBODIMENTS

First Embodiment

Figure 1:
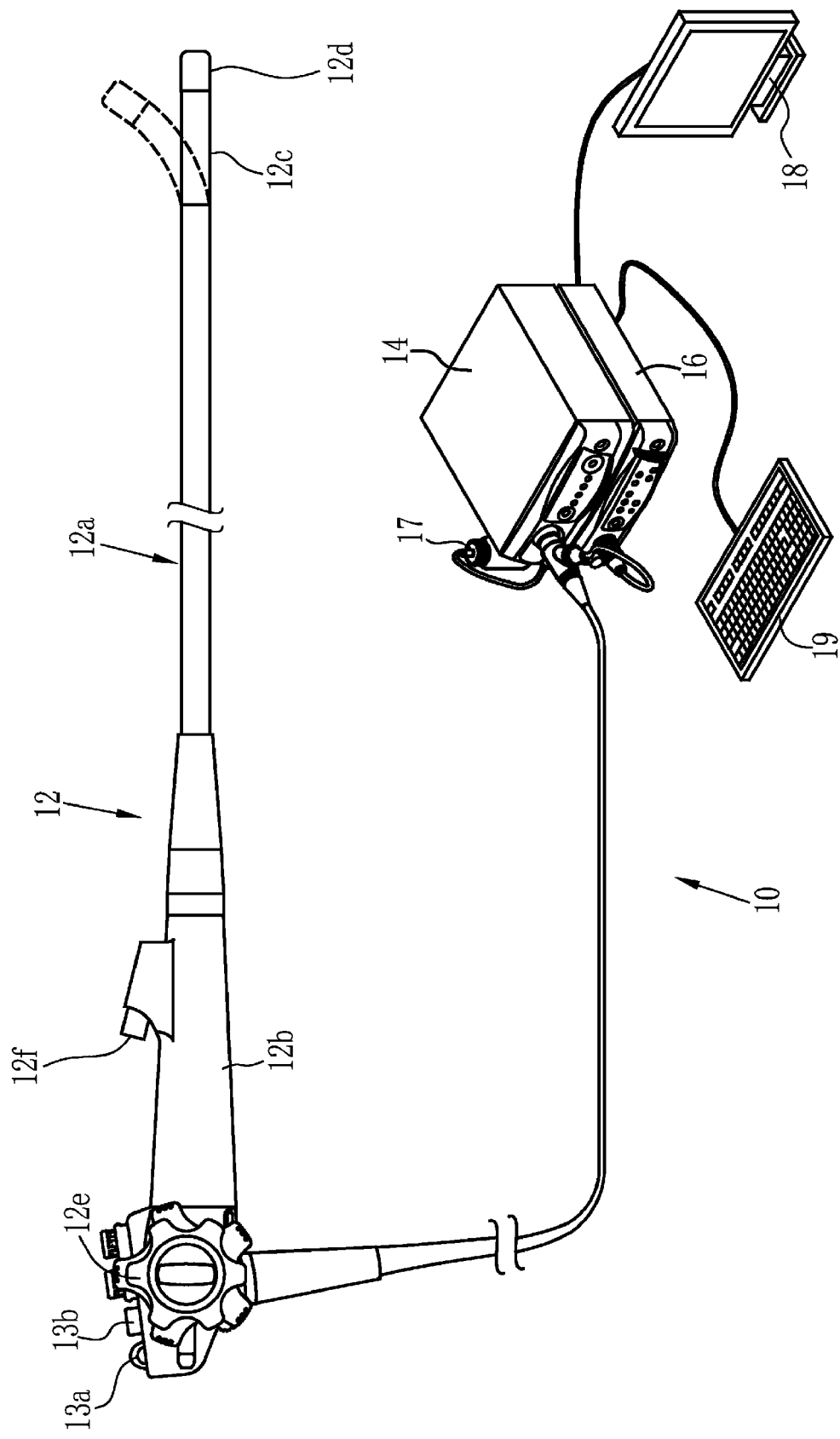
FIG. 1 is an external view of an endoscope system.

As illustrated in FIG. 1, an endoscope system 10 (endoscope apparatus) includes an endoscope 12, a light source device 14, a processor device 16, a monitor 18, and a console 19. The endoscope 12 captures an image of a photographic subject. The light source device 14 generates illumination light. The processor device 16 performs, for example, system control and image processing of the endoscope system 10. The monitor 18 is a display unit that displays, for example, an image captured by the endoscope 12. The console 19 is an input device for, for example, inputting settings to, for example, the processor device 16.

The endoscope 12 has an insertion part 12a that is inserted into a subject, an operation part 12b that is provided on the proximal end part of the insertion part 12a, a bending part 12c that is provided on the distal end side of the insertion part 12a, and a tip part 12d. When an angle knob 12e of the operation part 12b is operated, the bending part 12c bends. As a result, the tip part 12d turns in a desired direction. In addition to the angle knob 12e, the operation part 12b is provided with a treatment tool insertion port 12f, a zoom operation part 13a, and a water supply button 13b. The treatment tool insertion port 12f is a port through which a treatment tool, such as biopsy forceps, a snare, or an electric scalpel, is inserted. A treatment tool inserted through the treatment tool insertion port 12f protrudes from the tip part 12d. When the zoom operation part 13a is operated, an enlarged or reduced image of a photographic subject is captured. When the water supply button 13b is operated, a liquid, such as water, stored in a water supply tank 17 gushes out of the tip part 12d.

Figure 2:
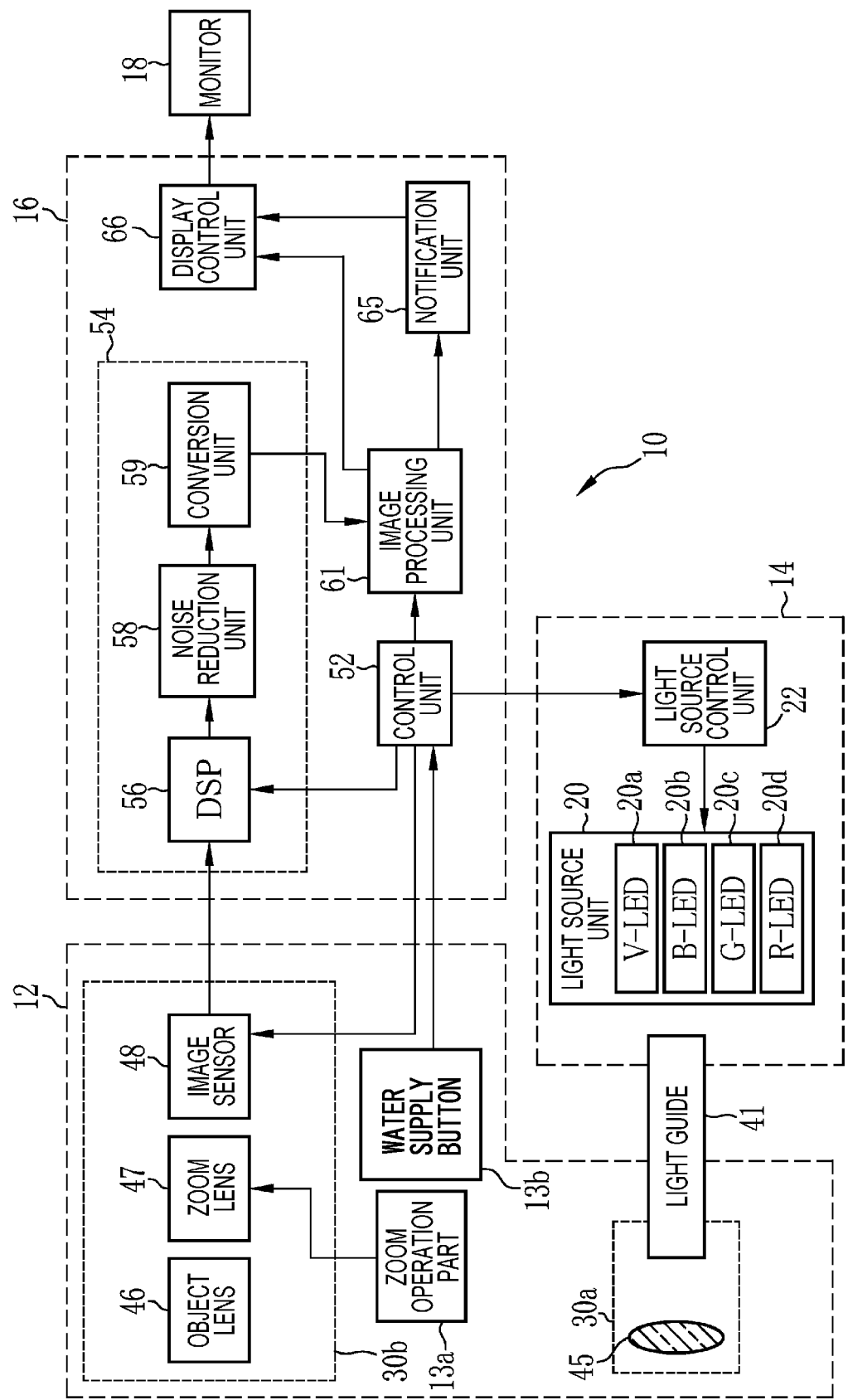
FIG. 2 is a block diagram of the endoscope system.

As illustrated in FIG. 2, the light source device 14 includes a light source unit 20 that emits illumination light and a light source control unit 22 that controls operations of the light source unit 20.

The light source unit 20 emits illumination light that illuminates a photographic subject. Emission of illumination light includes emission of, for example, excitation light that is used to emit illumination light. The light source unit 20 includes a light source formed of, for example, a laser diode (hereinafter referred to as an LD), an LED (light emitting diode), a xenon lamp, or a halogen lamp and emits at least illumination light in a white color or excitation light that is used to emit illumination light in the white color. The white color includes a pseudo white color that is substantially equivalent to a white color in image capturing of a photographic subject using the endoscope 12. The light source unit 20 includes, for example, a fluorescent body that emits light when irradiated with excitation light or an optical filter for adjusting, for example, the wavelength range, spectrum, or amount of light of the illumination light or excitation light as necessary. In addition, the light source unit 20 can emit light having a specific wavelength range necessary for capturing an image that is used to calculate biological information, such as the oxygen saturation of hemoglobin contained in the photographic subject.

In this embodiment, the light source unit 20 has LEDs in four colors, namely, a V-LED 20a, a B-LED 20b, a G-LED 20c, and an R-LED 20d. The V-LED 20a emits violet light VL having a center wavelength of 405 nm and a wavelength range of 380 to 420 nm. The B-LED 20b emits blue light BL having a center wavelength of 460 nm and a wavelength range of 420 to 500 nm. The G-LED 20c emits green light GL having a wavelength range of 480 to 600 nm. The R-LED 20d emits red light RL having a center wavelength of 620 to 630 nm and a wavelength range of 600 to 650 nm. The center wavelengths of the V-LED 20a and the B-LED 20b have a width of about 20 nm, and preferably, about 5 nm to about 10 nm.

The light source control unit 22 controls, for example, the timing at which each light source that constitutes the light source unit 20 is turned on, turned off, or blocked and the amount of light emission of each light source. As a result, the light source unit 20 can emit a plurality of types of illumination light having different spectra. In this embodiment, the light source control unit 22 controls, for example, turning-on and turning-off of each of the LEDs 20a to 20d, the amounts of light emission during turning-on, and insertion and removal of the optical filter by inputting independent control signals to the LEDs 20a to 20d to thereby adjust the spectrum of illumination light. Accordingly, the light source unit 20 emits white light. The light source unit 20 can at least emit illumination light formed of violet light in a narrow band. The "narrow band" means a substantially single wavelength range in relation to the characteristics of the photographic subject and/or the spectral characteristics of color filters of an image sensor 48. For example, in a case where light has a wavelength range of, for example, about ±20 nm or less (preferably, about ±10 nm or less) with reference to the center wavelength, the light is in a narrow band.

In the tip part 12d of the endoscope 12, an illumination optical system 30a and an imaging optical system 30b are provided. Illumination light from the light source unit 20 is propagated to the illumination optical system 30a through a light guide 41. The illumination optical system 30a has an illumination lens 45, and illumination light is emitted toward a photographic subject via the illumination lens 45.

The imaging optical system 30b has an object lens 46, a zoom lens 47, and the image sensor 48. The image sensor 48 captures an image of a photographic subject by using, for example, reflected light (in addition to the reflected light, scattered light, fluorescent light emitted from the photographic subject, or fluorescent light caused by a drug administered to the photographic subject is included) resulting from illumination light and returning from the photographic subject via the object lens 46 and the zoom lens 47. The zoom lens 47 moves in response to an operation of the zoom operation part 13a to enlarge or reduce an image of the photographic subject.

The image sensor 48 has, for each pixel, a color filter in one color among color filters in a plurality of colors. In this embodiment, the image sensor 48 is a color sensor having color filters in primary colors. Specifically, the image sensor 48 has R pixels each having a red filter (R filter), G pixels each having a green filter (G filter), and B pixels each having a blue filter (B filter).

Note that as the image sensor 48, a CCD (charge-coupled device) sensor or a CMOS (complementary metal-oxide semiconductor) sensor can be used. Although the image sensor 48 of this embodiment is a primary color sensor, a complementary color sensor can also be used. A complementary color sensor has, for example, cyan pixels each of which is provided with a cyan filter, magenta pixels each of which is provided with a magenta filter, yellow pixels each of which is provided with a yellow filter, and green pixels each of which is provided with a green filter. In a case where a complementary color sensor is used, an image obtained from the above-described pixels in the respective colors can be converted to an image similar to an image obtained by using a primary color sensor by performing conversion from complementary colors to primary colors. The same applies to a primary color sensor or a complementary color sensor having one or more types of pixels, such as W pixels (white pixels that receive light in substantially all wavelength ranges), having characteristics other than the above. Although the image sensor 48 of this embodiment is a color sensor, a monochrome sensor having no color filters may be used.

The processor device 16 has a control unit 52, an image obtaining unit 54, an image processing unit 61, a notification unit 65, and a display control unit 66 (see FIG. 2).

The control unit 52 centrally controls the endoscope system 10 and controls, for example, synchronization between the timing of irradiation with illumination light and the timing of image capturing. In a case where, for example, various settings are input by using, for example, the console 19, the control unit 52 inputs the settings to the respective units of the endoscope system 10, such as the light source control unit 22, the image sensor 48, and the image processing unit 61.

The image obtaining unit 54 obtains a captured image of a photographic subject. More specifically, the image obtaining unit 54 obtains from the image sensor 48 an image obtained by image capturing of a photographic subject using the pixels in the respective colors, that is, a raw image. The raw image is an image that is not yet subjected to demosaicing. An image obtained from the image sensor 48 and subjected to a process, such as a noise reducing process, is also a raw image as long as the image is not yet subjected to demosaicing.

The image obtaining unit 54 includes a DSP (digital signal processor) 56, a noise reduction unit 58, and a conversion unit 59 that perform various processes for the obtained raw image as necessary to generate an endoscopic image.

The DSP 56 includes, for example, an offset processing unit, a defect correction processing unit, a demosaicing processing unit, an interpolation processing unit, a linear matrix processing unit, and a YC conversion processing unit (none of which are illustrated). The DSP 56 uses these units to perform various processes for a raw image or an image generated by using a raw image.

The offset processing unit performs an offset process for a raw image. The offset process is a process for reducing dark current components in a raw image to set an accurate zero level. The offset process may be called a clamping process. The defect correction processing unit performs a defect correction process for a raw image. The defect correction process is a process for, in a case where the image sensor 48 includes a pixel (defective pixel) having a defect caused by a manufacturing process or by aging, correcting or generating the pixel value of a raw pixel corresponding to the defective pixel of the image sensor 48. The demosaicing processing unit performs a demosaicing process for raw images in the respective colors corresponding to the respective color filters. The demosaicing process is a process for generating a pixel value, of a raw image, that is missing due to the arrangement of the color filters, by interpolation. The linear matrix processing unit performs a linear matrix process for an endoscopic image generated by allocating one or more raw images to R, G, and B channels. The linear matrix process is a process for increasing the color reproducibility of the endoscopic image. The YC conversion processing unit performs a process for converting the endoscopic image generated by allocating one or more raw images to the R, G, and B channels to an endoscopic image having a luminance channel Y, a color difference channel Cb, and a color difference channel Cr.

The noise reduction unit 58 performs a noise reduction process for the endoscopic image having the luminance channel Y, the color difference channel Cb, and the color difference channel Cr by using, for example, a moving average method or a median filtering method. The conversion unit 59 reconverts the endoscopic image having the luminance channel Y, the color difference channel Cb, and the color difference channel Cr and subjected to the noise reduction process to an endoscopic image having the channels of the respective colors of R, G, and B.

Figure 3:
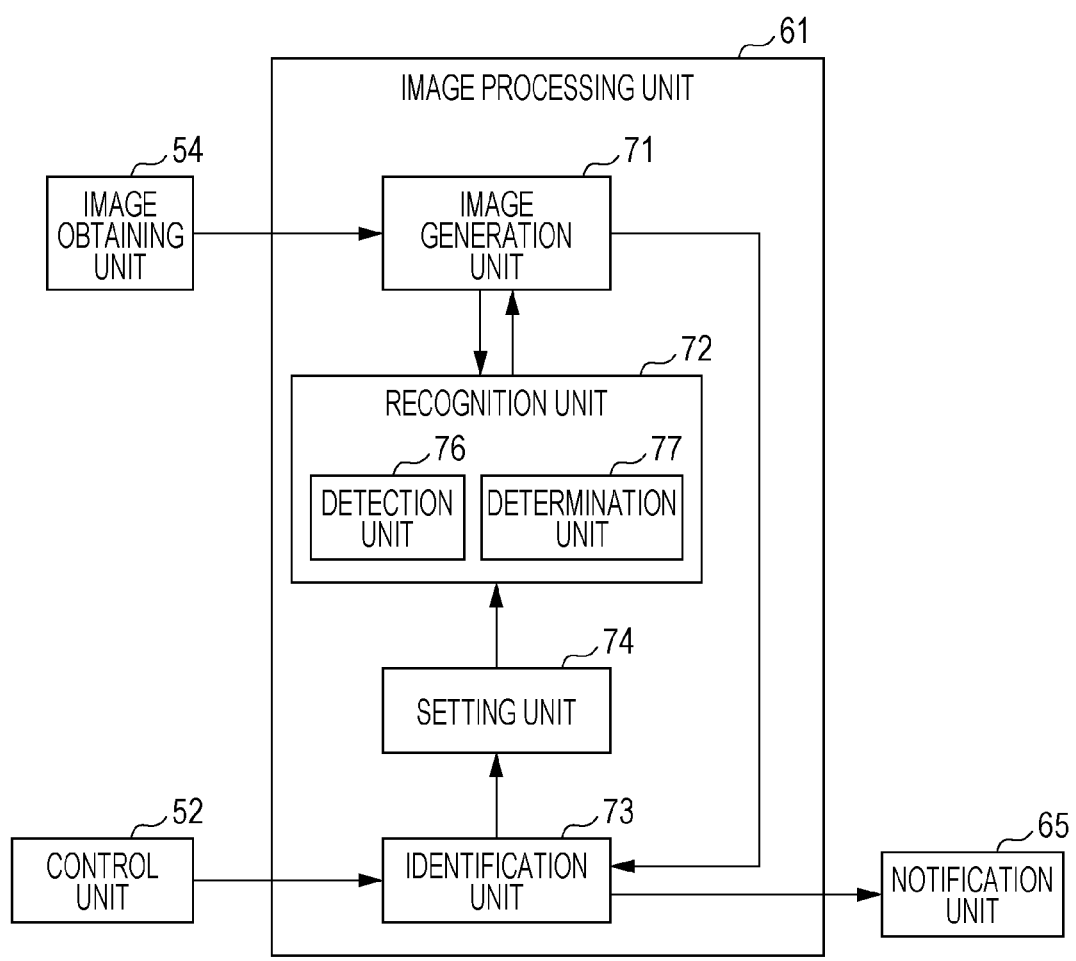
FIG. 3 is a block diagram of an image processing unit.

The image processing unit 61 performs for an endoscopic image output by the image obtaining unit 54, necessary image processing. The image processing unit 61 uses the endoscopic image to perform a recognition process of recognizing a photographic subject having specific characteristics or part of the photographic subject. Specifically, as illustrated in FIG. 3, the image processing unit 61 includes, for example, an image generation unit 71, a recognition unit 72, an identification unit 73, and a setting unit 74.

The image generation unit 71 obtains an endoscopic image from the image obtaining unit 54 and generates an endoscopic image that is used in, for example, display on the monitor 18. For example, the image generation unit 71 obtains from the image obtaining unit 54 a B image obtained by image capturing of a photographic subject using the B pixels, a G image obtained by image capturing of the photographic subject using the G pixels, and an R image obtained by image capturing of the photographic subject using the R pixels and uses all or some of the images to generate an endoscopic image for display.

When generating an endoscopic image for display, the image generation unit 71 performs for an endoscopic image obtained from the image obtaining unit 54 or for an image generated by using an endoscopic image obtained from the image obtaining unit 54, necessary image processing. The image processing performed by the image generation unit 71 is, for example, a highlighting process of highlighting a photographic subject or part of the photographic subject. Highlighting means to distinguish a specific part from, for example, the other tissue or structures to allow obtaining of information about the specific part. For example, a process for outlining a part having specific characteristics with a frame to display the outline or a process for, for example, changing the color or brightness of the part having specific characteristics relative to the other parts (for example, a normal mucous membrane) is the highlighting process. "Allowing obtaining of information about the specific part" includes allowing recognition of, for example, the position, shape, color or brightness, and/or size (area) of the specific part and also includes allowing knowing or obtaining of biological function information (for example, the oxygen saturation or the blood vessel concentration) about the specific part.

The recognition unit 72 performs the recognition process of recognizing a photographic subject by using an image obtained by image capturing of the photographic subject. "Recognizing a photographic subject" means to detect the presence or absence of a part of a photographic subject having specific characteristics (including a case of detecting the entire photographic subject), determine the type or the degree of progression of a part of a photographic subject having specific characteristics (including determination of the entire photographic subject), and/or obtain (for example, calculate) biological function information about a photographic subject in part or in whole. A part of a photographic subject having specific characteristics is, for example, a lesion, a potential lesion, or a treatment scar, which is a scar from a treatment (hereinafter referred to as a lesion or the like). That is, the recognition unit 72 can recognize the presence or absence of a lesion or the like by the recognition process. Further, the recognition unit 72 can recognize the type or the degree of progression of a lesion or the like by the recognition process. Recognition of the type of a lesion or the like means, for example, in a case where the lesion or the like is a polyp, to determine the type, such as adenoma, hypertrophic polyp, or cancer. Recognition of the degree of progression of a lesion or the like means, for example, in a case where the lesion or the like is cancer, to determine the stage of the cancer or determine, for example, the NICE (NBI (Narrow-Band Imaging) International Colorectal Endoscopic) classification or the JNET (The Japan NBI Expert Team) classification. In this embodiment, an image obtained by image capturing of a photographic subject is an endoscopic image obtained from the image obtaining unit 54 or an endoscopic image generated by the image generation unit 71. Further, in this embodiment, the recognition unit 72 detects a lesion or the like by the recognition process.

The recognition unit 72 is, for example, an artificial intelligence (AI) having a learning function. Specifically, the recognition unit 72 is an AI trained by using a machine learning algorithm, such as a neural network (NN), a convolutional neural network (CNN), AdaBoost, or a random forest. Further, the recognition unit 72 is trained using specific images in order to perform the recognition process, and therefore, even if the recognition unit 72 can perform the recognition process using the other images, the accuracy of the result of the recognition process may be low. In this embodiment, the recognition unit 72 is an AI trained to detect lesions or the like using endoscopic images. "Having a learning function" means to have an ability to learn and includes a trained state. Note that the recognition unit 72 might not be configured as an AI and can be configured to calculate a feature value from an image and to, for example, perform detection by using the calculated feature value.

In this embodiment, the recognition unit 72 includes a detection unit 76 and a determination unit 77. The detection unit 76 is an AI trained to detect lesions or the like using endoscopic images. The determination unit 77 is an AI trained to determine the degrees of progression of lesions or the like using endoscopic images.

The recognition unit 72 inputs the result of the recognition process to the image generation unit 71 or to the display control unit 66 in accordance with the details of the recognition process. When the recognition unit 72 inputs the result of the recognition process to the image generation unit 71, the image generation unit 71 generates an endoscopic image for display that reflects the result of the recognition process. When the recognition unit 72 inputs the result of the recognition process to the display control unit 66, the display control unit 66 displays the result of the recognition process on the screen of the monitor 18 together with the endoscopic image obtained from the image generation unit 71. The recognition unit 72 inputs the result of the recognition process to the image generation unit 71 in a case where, for example, the color of the endoscopic image for display is changed in accordance with a value of biological function information, which is the result of the recognition process. The recognition unit 72 inputs the result of the recognition process to the display control unit 66 in a case where, for example, the position of a lesion or the like, which is the result of the recognition process, is to be indicated by, for example, displaying a frame that is superimposed on the endoscopic image. In this embodiment, the recognition unit 72 inputs information about, for example, the position of a detected lesion or the like, which is the result of the recognition process, to the image generation unit 71. The image generation unit 71 generates an endoscopic image for display for which the highlighting process is performed for a part in which the lesion or the like is present.

The identification unit 73 identifies an operation performed on a photographic subject. An operation performed on a photographic subject means an act that exerts some (desired) effects on a photographic subject. Examples of an operation performed on a photographic subject include surgical operations or treatments related to therapies, such as removal of tissue from a living body for use in a biopsy or endoscopic mucosal resection (EMR), spraying of a liquid on a photographic subject, and cleaning of a photographic subject. Spraying of a liquid on a photographic subject means to administer a liquid drug to a photographic subject or spray water. Spraying of water means to pour water over a photographic subject in part or in whole. Administration of a drug includes spraying of, for example, a coloring agent, such as indigo carmine, on a photographic subject and also includes intravenous injection of a fluorescent drug, such as indocyanine green (ICG), into a photographic subject. Cleaning of a photographic subject means to remove, for example, substances, such as a residual substance, a residual liquid, or blood, which are adhered to the photographic subject and hinder observation, by, for example, water or air so as to make the photographic subject that is to be observed visible to the endoscope 12. An act that can exert an effect on a photographic subject is included in an "operation performed on a photographic subject" even if no effect is exerted on the photographic subject as a result of the act. For example, an act of jetting air in order to clean a photographic subject is an operation performed on the photographic subject even if the photographic subject does not become clean as a result of the act. An "operation performed on a photographic subject" includes a series of related acts before and after an effect is exerted on the photographic subject. For example, an act of making forceps protrude from the endoscope 12 in a case of a biopsy is included in a series of acts related to the biopsy even if the act is performed before removal of tissue, and is included in an operation performed on the photographic subject.

Identification of an operation performed on a photographic subject means to detect an operation to be performed on a photographic subject or to detect an operation that has been performed on a photographic subject. An operation is identified by, for example, detecting use of a treatment tool, detecting a treatment scar (in addition to detection of a scar from a surgical operation, for example, detection of bleeding caused by a treatment and detection of tissue or a structure for which, for example, the color has changed as a result of, for example, spraying of a coloring agent are included), or detecting an operation of, for example, the water supply button 13b. Regarding use of a treatment tool, the identification unit 73 can detect the presence or absence of a treatment tool or the type (for example, the shape) of a treatment tool by using, for example, an endoscopic image or setting information. The identification unit 73 can detect, for example, a treatment tool (including spraying of water) as described above by analyzing an endoscopic image. Further, the identification unit 73 can detect an operation of, for example, the water supply button 13b by obtaining a signal or setting information from the control unit 52.

Identification of an operation performed on a photographic subject includes determination of whether or not an operation is performed on a photographic subject and identification of the type of an operation performed on a photographic subject. Determination of whether or not an operation is performed includes detection of an "operation performed on a photographic subject", which is a detection target, regardless of the type of operation. Identification of the type of operation performed on a photographic subject means to identify an operation performed on a photographic subject by identifying the details of the operation in a distinguished manner (for example, whether the operation is a biopsy or administration of a drug). In this embodiment, the identification unit 73 determines whether or not an operation is performed on a photographic subject.

The setting unit 74 enables or disables the recognition unit 72 in accordance with the result of identification by the identification unit 73. The result of identification by the identification unit 73 is whether or not an operation is performed on the photographic subject and/or the type of operation performed on the photographic subject. "Enabling the recognition unit 72" means to enable the recognition process that is performed by the recognition unit 72, thereby performing setting so as to allow the recognition unit 72 to perform the recognition process, to allow a notification of the result of the recognition process to be given, or to allow the recognition unit 72 to output the result of the recognition process. "Disabling the recognition unit 72" means to disable the recognition process that is performed by the recognition unit 72, thereby performing setting so as not to allow the recognition unit 72 to perform the recognition process, not to allow a notification of the result of the recognition process to be given, or not to allow the recognition unit 72 to output the result of the recognition process. That is, "enabling or disabling the recognition unit 72" means to enable or disable the recognition process that is performed by the recognition unit 72 or enable or disable giving of a notification of the result of the recognition process (or output of the result of the recognition process). "Giving of a notification of the result of the recognition process" means to make the result of the recognition process recognizable by a doctor or the like. "Output of the result of the recognition process" means to pass, by the recognition unit 72, the result of the recognition process to, for example, the other processing units, such as the image generation unit 71 and so on. In this embodiment, the setting unit 74 enables or disables the recognition process itself that is performed by the recognition unit 72.

When the identification unit 73 determines whether or not an operation is performed on a photographic subject, the setting unit 74 disables the recognition unit 72 in a case where an operation is performed on the photographic subject, and enables the recognition unit 72 in a case where no operation is performed on the photographic subject. This is because the case where an operation is performed on the photographic subject is a situation where the accuracy of the recognition process may decrease or the doctor or the like needs to concentrate on their operation.

When the identification unit 73 identifies the type of operation performed on a photographic subject, the setting unit 74 disables the recognition unit 72 in a case where a specific operation is performed on the photographic subject. The specific operation means an operation that decreases the accuracy of the recognition process that is performed by the recognition unit 72 or an operation on which the doctor or the like needs to concentrate. Therefore, when the identification unit 73 identifies the type of operation performed on the photographic subject, the setting unit 74 can enable the recognition unit 72 depending on the type of operation. Accordingly, appropriate diagnosis support can be continuously provided in accordance with the situation.

In a case where the recognition unit 72 performs a plurality of types of recognition processes, the setting unit 74 can enable or disable each of the recognition processes. For example, in a case where the setting unit 74 enables or disables the recognition unit 72, the setting unit 74 can enable or disable the detection unit 76 and enable or disable the determination unit 77 regardless of whether the detection unit 76 is enabled or disabled. As a matter of course, the setting unit 74 can enable or disable the recognition unit 72 as a whole including both the detection unit 76 and the determination unit 77. In this embodiment, the setting unit 74 enables or disables the recognition unit 72 as a whole, namely, including both the detection unit 76 and the determination unit 77.

The notification unit 65 obtains, for example, the result of identification from the identification unit 73 (or obtains information about setting of the recognition unit 72 from the setting unit 74) and gives a notification of whether the recognition unit 72 is enabled or disabled. "Giving a notification" of whether the recognition unit 72 is enabled or disabled means to allow the doctor or the like, who is a user, to know whether the recognition unit 72 is enabled or disabled. For example, the notification unit 65 can give a notification of whether the recognition unit 72 is enabled or disabled by displaying or not displaying on the screen of the monitor 18, for example, a message (character string), a letter, a geometric shape, and/or a symbol (including display of, for example, a mark, an icon, or an indicator) or by changing the display. In addition, the notification unit 65 can give a notification of whether the recognition unit 72 is enabled or disabled by, for example, lighting, extinguishing, or blinking a lamp, a sound (including voice), or vibrating a member having a vibration function, or by changing these. As a matter of course, the notification unit 65 can give a notification of whether the recognition unit 72 is enabled or disabled by combining, for example, a character string and lighting of a lamp. In this embodiment, the notification unit 65 performs display on the screen of the monitor 18 indicating whether the recognition unit 72 is enabled or disabled.

The display control unit 66 converts an endoscopic image output by the image processing unit 61 to an endoscopic image in a form suitable for display and outputs the endoscopic image to the monitor 18. Then, the monitor 18 displays the endoscopic image. In this embodiment, the notification unit 65 inputs information indicating whether the recognition unit 72 is enabled or disabled to the display control unit 66. Then, the display control unit 66 displays the information on the screen of the monitor 18.

Figure 4:
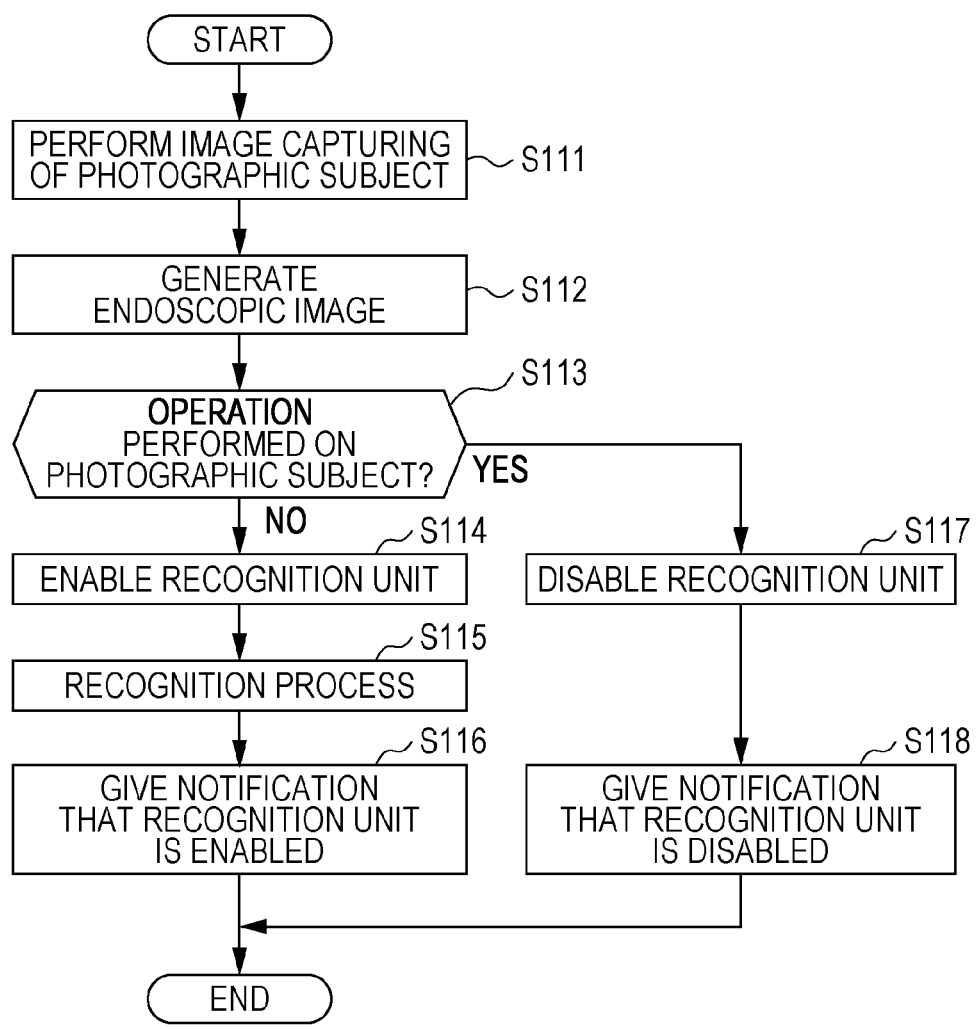
FIG. 4 is a flowchart illustrating an operation form of the endoscope system.

The endoscope system 10 configured as described above operates as follows to give a notification of whether the recognition unit 72 is enabled or disabled. As illustrated in FIG. 4, when a doctor or the like performs image capturing of a photographic subject by using the endoscope 12 (step S111), the image obtaining unit 54 obtains an endoscopic image. The image generation unit 71 performs necessary image processing and generates an endoscopic image for display (step S112).

Figure 5:
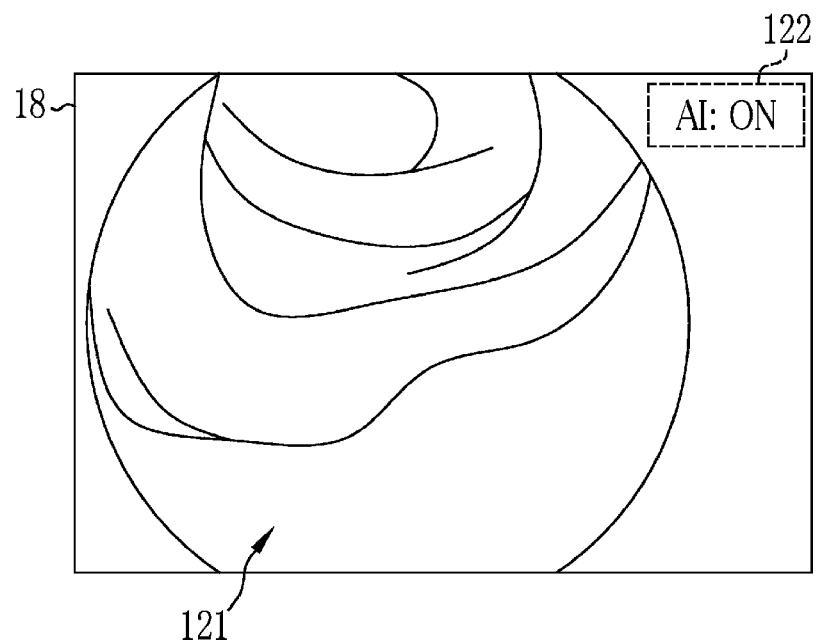
FIG. 5 illustrates an example of display in a case where a recognition unit is enabled.
Figure 6:
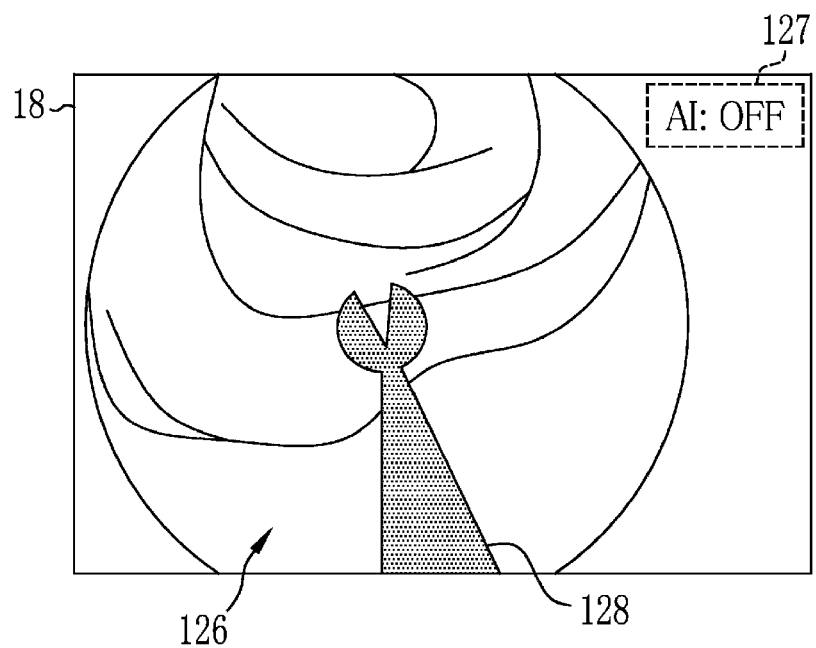
FIG. 6 illustrates an example of display in a case where the recognition unit is disabled.

Thereafter or concurrently with generation of an endoscopic image for display, the identification unit 73 identifies an operation performed on the photographic subject by using, for example, the endoscopic image for display (step S113). In a case where no operation is performed on the photographic subject (NO in step S113), the setting unit 74 enables the recognition unit 72 (step S114). Then, the recognition unit 72 performs the recognition process for, for example, the endoscopic image for display (step S115). In this embodiment, the recognition unit 72 includes the detection unit 76 and the determination unit 77, and the setting unit 74 enables or disables these units as a whole, and therefore, in the case where no operation is performed on the photographic subject, the recognition unit 72 performs recognition processes for both detection and determination of a lesion or the like. Thereafter, the recognition unit 72 outputs the results of recognition to the image generation unit 71, and the image generation unit 71 uses the results of recognition to generate an endoscopic image for display in which, for example, a lesion or the like is highlighted and outputs the endoscopic image to the display control unit 66. Then, the monitor 18 displays the endoscopic image on the screen. The notification unit 65 gives a notification that the recognition unit 72 is enabled (step S116). Here, the setting unit 74 enables the recognition unit 72, and therefore, the notification unit 65 displays on the screen of the monitor 18, for example, a character string indicating that the recognition unit 72 is enabled. For example, as illustrated in FIG. 5, the notification unit 65 displays display 122 "AI: ON" on the screen of the monitor 18 on which an endoscopic image 121 is displayed. Accordingly, the notification unit 65 gives a notification that the recognition unit 72 is enabled. Note that the endoscopic image 121 is an image representing that no operation is performed on the photographic subject and that no lesion or the like is present On the other hand, in a case where the identification unit 73 detects an operation performed on the photographic subject (YES in step S113), the setting unit 74 disables the recognition unit 72 (step S117). Then, the recognition unit 72 does not perform detection or determination, and the image generation unit 71 outputs the generated endoscopic image for display to the display control unit 66. Then, the monitor 18 displays the endoscopic image on the screen. The notification unit 65 gives a notification that the recognition unit 72 is disabled (step S118). For example, as illustrated in FIG. 6, the notification unit 65 displays display 127 "AI: OFF" on the screen of the monitor 18 on which an endoscopic image 126 is displayed. Accordingly, the notification unit 65 gives a notification that the recognition unit 72 is disabled. Note that in the endoscopic image 126, biopsy forceps 128 are present. Therefore, the recognition unit 72 is disabled.

As described above, in the endoscope system 10, the identification unit 73 identifies an operation performed on the photographic subject, and the setting unit 74 enables or disables the recognition unit 72 in accordance with the result of identification by the identification unit 73. Accordingly, the endoscope system 10 enables or disables the recognition unit 72 in accordance with the situation of observation, and therefore, the doctor or the like, who is a user, need not manually enable or disable the recognition unit 72 by themselves during the observation, which is convenient therefor. However, when the recognition unit 72 is only automatically enabled or disabled, a doctor or the like may incorrectly recognize the result of performing the recognition process or the result of not performing the recognition process. For example, in a case where a doctor or the like has a preconception that the recognition unit 72 is enabled, when the recognition unit 72 is automatically disabled and the result of the recognition process is not displayed any more, even if a lesion or the like is present, the doctor or the like may incorrectly recognize that no lesion or the like is present as a result of the recognition unit 72 performing the recognition process. Therefore, in the endoscope system 10, the notification unit 65 gives a notification of whether the recognition unit 72 is enabled or disabled. Accordingly, when the doctor or the like sees the display 122 "AI: ON" or the display 127 "AI: OFF", it is obvious to the doctor or the like that the recognition unit 72 is performing the recognition process or not performing the recognition process, which can prevent incorrect recognition as described above. As a consequence, it is possible to prevent wrong diagnoses.

Second Embodiment

Figures 7, 8:
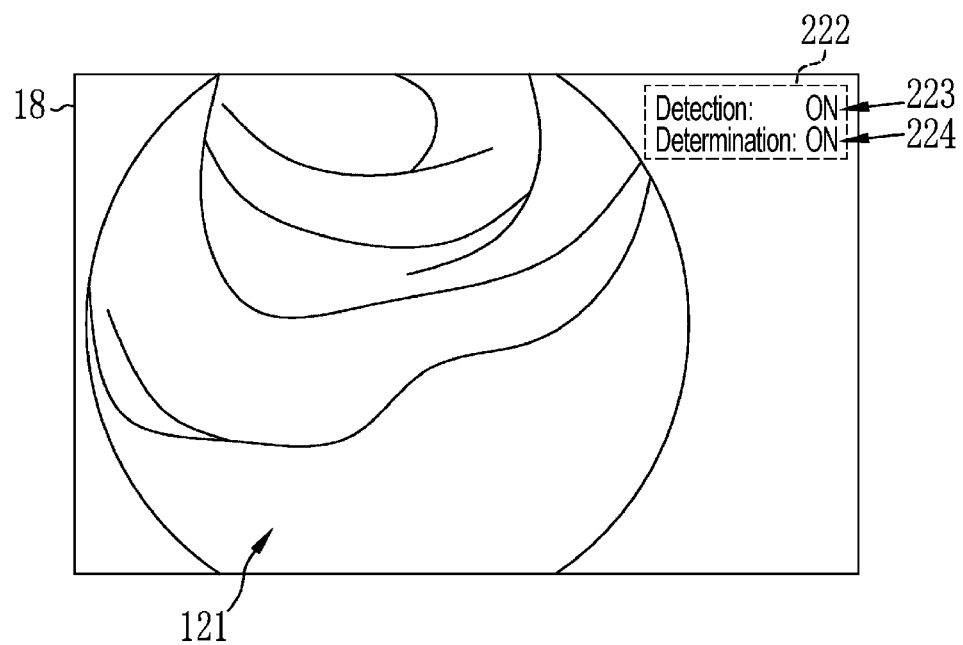
FIG. 7 illustrates an example of display of a second embodiment.
FIG. 8 is a table indicating operation states of detection and determination.

In a case where the setting unit 74 enables or disables each of the recognition processes, the notification unit 65 can give a notification, for each recognition process, of whether the recognition process is enabled or disabled. For example, in a case where the recognition unit 72 has the detection unit 76 and the determination unit 77 and where the setting unit 74 enables or disables the detection unit 76 and the determination unit 77 independently of each other, as illustrated in FIG. 7, the notification unit 65 can display in a display field 222 showing whether the recognition unit 72 is enabled or disabled, display 223 indicating whether the detection unit 76 is enabled or disabled and display 224 indicating whether the determination unit 77 is enabled or disabled to thereby give a notification of the states of these units. For example, the display 223 "Detection: ON" indicates that the detection unit 76 is enabled, and display "Detection: OFF" (not illustrated) indicates that the detection unit 76 is disabled. Similarly, the display 224 "Determination: ON" indicates that the determination unit 77 is enabled, and display "Determination: OFF" (not illustrated) indicates that the determination unit 77 is disabled.

As described above, in a case where the setting unit 74 enables or disables each of the recognition processes, the setting unit 74 can enable a recognition process that is appropriate to the situation of observation and disable the other recognition process. Accordingly, the endoscope system 10 can provide optimum diagnosis support. Then, the notification unit 65 gives a notification, for each recognition process, whether the recognition process is enabled or disabled, and therefore, the doctor or the like can accurately grasp whether each recognition process is enabled or disabled. Accordingly, it is possible to prevent incorrect recognition of the result of performing the recognition process and the result of not performing the recognition process. As a consequence, it is possible to prevent wrong diagnoses.

In the second embodiment described above, an example where both the detection unit 76 and the determination unit 77 are enabled is illustrated. As illustrated in FIG. 8, depending on the identification state of the identification unit 73, it may be appropriate to enable only the detection unit 76, it may be appropriate to enable only the determination unit 77, or it may be appropriate to disable both the detection unit 76 and the determination unit 77.

"Identification state 1" is a state where it is appropriate to enable both the detection unit 76 and the determination unit 77 and corresponds to, for example, a case where no operation is performed on the photographic subject or a case where the photographic subject is cleaned by using, for example, water. In these cases, it is highly likely that detection and determination of a lesion or the like are required.

"Identification state 2" is a state where it is appropriate to enable the detection unit 76 and disable the determination unit 77. For example, this state corresponds to a case where, when a doctor or the like performs, for example, a biopsy or a surgical operation, bleeding from the photographic subject is an identification target (detection target) of the identification unit 73, that is, corresponds to a situation where detection of bleeding is necessary in order to, for example, confirm stopping of bleeding but determination is not necessary because, for example, a surgical operation is already ongoing. The identification unit 73 can determine the above-described state in accordance with, for example, the type of operation performed on the photographic subject.

"Identification state 3" is a state where it is appropriate to disable the detection unit 76 and enable the determination unit 77. This state corresponds to, for example, a case where, for example, a lesion or the like has already been detected, redetection of the lesion or the like is not necessary, and the doctor or the like wants to receive more detailed diagnosis support from the endoscope system 10 in a diagnosis regarding the detected lesion or the like. Specifically, this state corresponds to a case where a coloring agent is sprayed on the photographic subject to determine the degree of progression of the lesion or the like. The identification unit 73 can determine the above-described state in accordance with, for example, the type of operation performed on the photographic subject.

"Identification state 4" is a state where it is appropriate to disable both the detection unit 76 and the determination unit 77. This state corresponds to, for example, a case where, for example, detection and determination of a lesion or the like are completed and the doctor or the like performs, for example, a biopsy or a surgical operation in which the doctor or the like needs to concentrate on their operation. The identification unit 73 can determine the above-described state in accordance with, for example, the type of operation. In a case where the identification unit 73 detects bleeding from the photographic subject, for example, the identification state of the identification unit 73 becomes identification state 2.

Note that in the second embodiment described above, whether the detection unit 76 and the determination unit 77 are enabled or disabled is indicated by "ON" or "OFF"; however, whether the detection unit 76 and the determination unit 77 are enabled or disabled can be indicated by the other display. For example, instead of the display "OFF", display such as "Unsupported" may be used. In a case where the detection unit 76 or the determination unit 77 is enabled but the accuracy (correctness or reliability) of the recognition process is low, display such as "Unsupported" can be displayed instead of the display "ON". For example, in identification state 3, in a case where the determination unit 77 does not support determination of a photographic subject on which a coloring agent is sprayed, the accuracy of determination decreases, and therefore, "Detection: OFF" and "Determination: Unsupported" can be displayed. Such changes and so on in the display form can be similarly made in the first embodiment.

Third Embodiment

In the first embodiment and the second embodiment described above, the notification unit 65 gives a notification of whether the recognition unit 72 is enabled or disabled; however, the notification unit 65 can further give a notification of whether or not an operation is performed or the type of operation identified by the identification unit 73.

That is, in addition to whether the recognition unit 72 is enabled or disabled, the notification unit 65 can give a notification of the result of identification by the identification unit 73.

Figure 9:
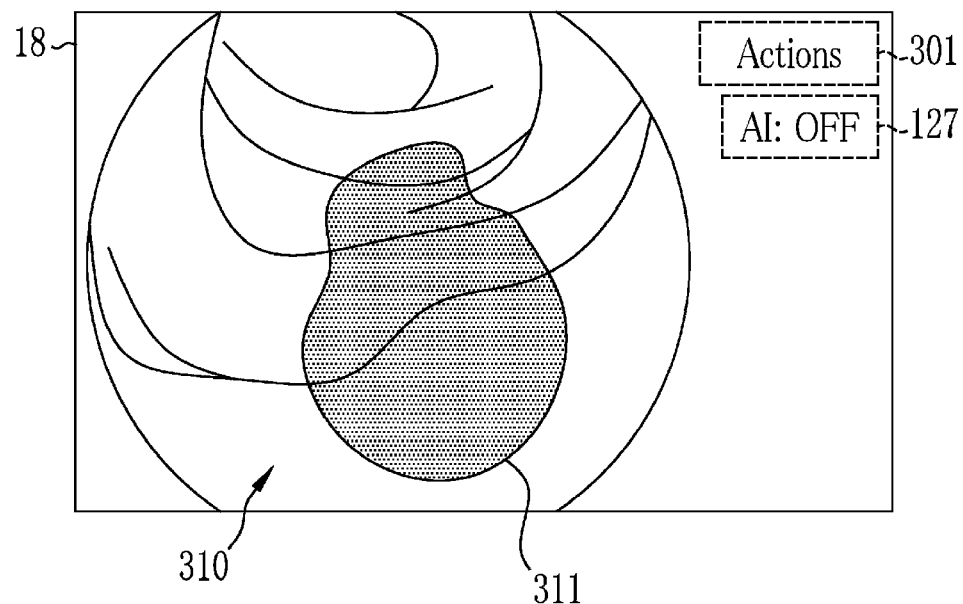
FIG. 9 is an example of display of a third embodiment.

For example, in a case where the identification unit 73 detects an operation performed on a photographic subject, the notification unit 65 can give a notification that an operation performed on the photographic subject is detected, by, for example, display 301 "Actions" ("Operation") in addition to a notification of whether the recognition unit 72 is enabled or disabled, such as the display 127 "AI: OFF", as illustrated in FIG. 9. Note that an endoscopic image 310 is an endoscopic image representing that a coloring agent 311 is sprayed on the photographic subject.

As described above, when the notification unit 65 gives a notification of whether or not an operation is performed on the photographic subject, the doctor or the like can recognize what causes the recognition unit 72 to be enabled or disabled. As a consequence, it is possible to prevent incorrect recognition of the result of performing the recognition process and the result of not performing the recognition process with more certainty and to prevent wrong diagnoses.

Figure 10:
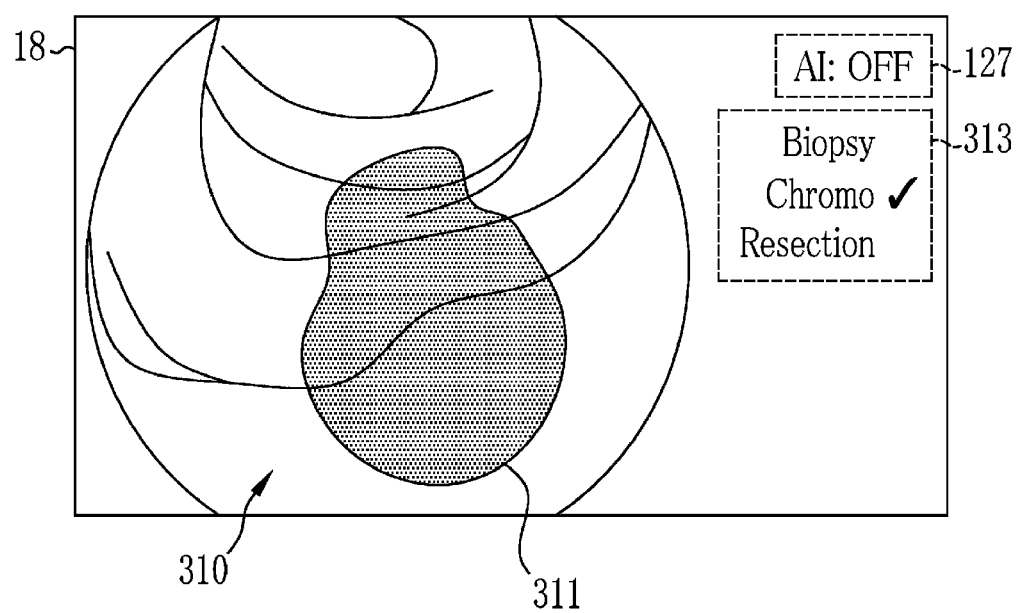
FIG. 10 is an example of display of the details of an operation.

The notification unit 65 can give a notification of the type of operation identified by the identification unit 73. For example, as illustrated in FIG. 10, the notification unit 65 can display "Biopsy" indicating a biopsy, "Chromo" indicating spraying of a coloring agent, and "Resection" indicating endoscopic mucosal resection in an operation type display field 313 in a list form and, for example, check the type of operation (in FIG. 10, "Chromo") identified by the identification unit 73 to thereby give a notification of the type of operation identified by the identification unit 73.

As described above, when the identification unit 73 identifies the type of operation and the notification unit 65 gives a notification of the type of operation identified by the identification unit 73, the doctor or the like can recognize in detail what causes the recognition unit 72 to be enabled or disabled. As a consequence, it is possible to prevent incorrect recognition of the result of performing the recognition process and the result of not performing the recognition process with more certainty and to prevent wrong diagnoses.

Note that a notification of whether or not an operation is performed on the photographic subject and the type of operation in the third embodiment described above is applicable to the case where, for each recognition process, a notification of whether the recognition process is enabled or disabled is given as in the second embodiment. In this case, the display field 222 showing whether the recognition unit 72 is enabled or disabled (see FIG. 7), and the display 301 "Actions" or the operation type display field 313 need to be displayed on the monitor 18.

Figure 11:
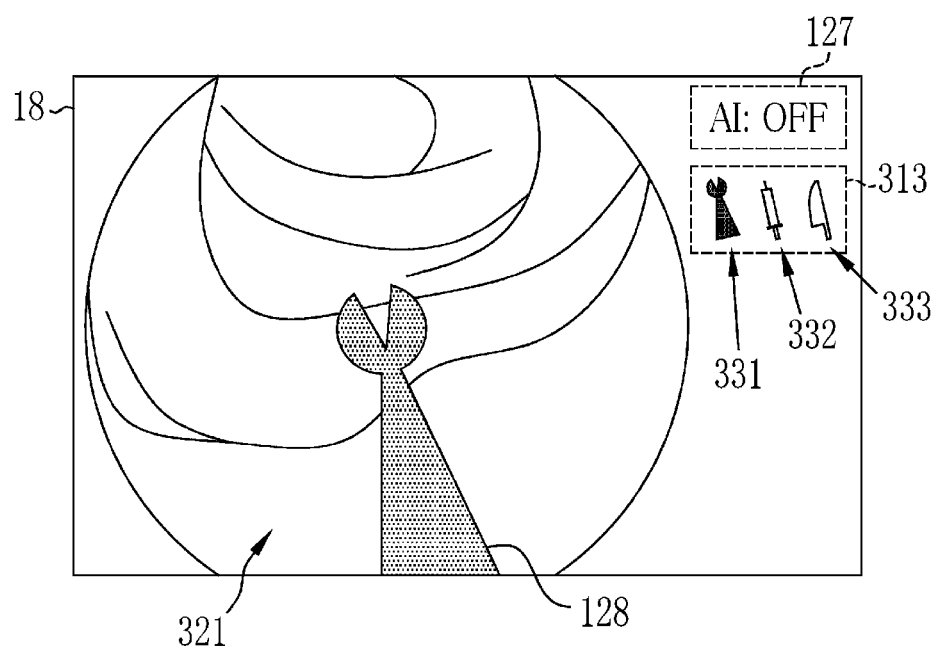
FIG. 11 is an example of display of the details of an operation.

In the third embodiment described above, the notification unit 65 can give a notification of whether or not an operation is performed on the photographic subject or the type of operation, by display other than display of a letter or a character string. For example, as illustrated in FIG. 11, an icon 331 indicating a biopsy, an icon 332 indicating spraying of a coloring agent, and an icon 333 indicating endoscopic mucosal resection can be displayed in the operation type display field 313 in a list form, and an icon corresponding to the type of operation identified by the identification unit 73 can be colored to thereby give a notification of the type of operation identified by the identification unit 73. Note that in FIG. 11, biopsy forceps 128 are present in an endoscopic image 321, and therefore, the icon 331 indicating a biopsy is colored.

Figure 12:
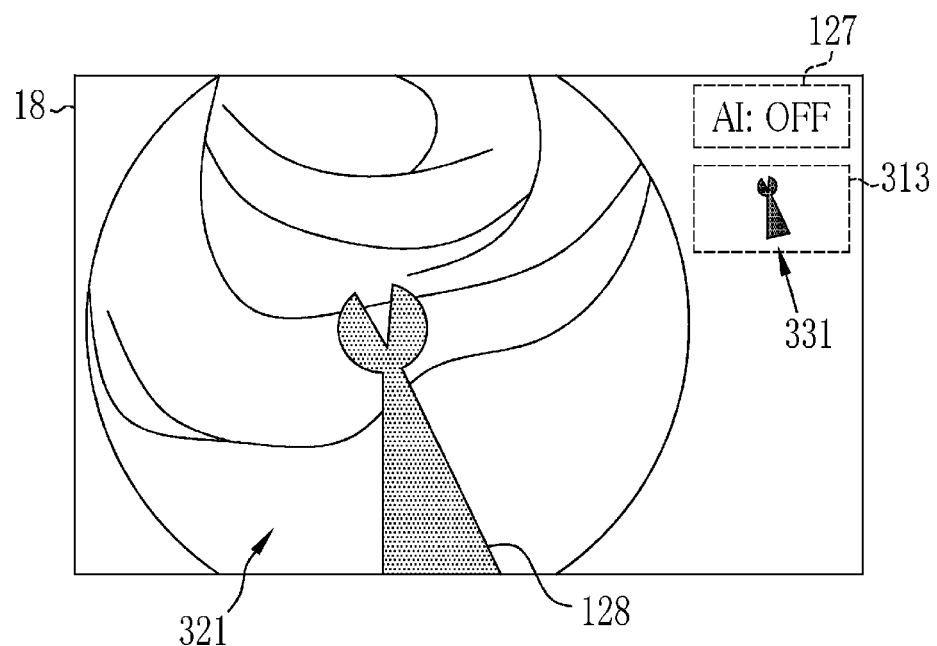
FIG. 12 is an example of display of the details of an operation.

As described above, in a case where the types of operations are indicated by icons, only an icon that corresponds to the type of operation identified by the identification unit 73 can be displayed in the operation type display field 313 as illustrated in FIG. 12. The same applies to a case where the types of operations performed on the photographic subject are indicated in the operation type display field 313 by character strings (see FIG. 10) and, for example, only a character string that indicates the type of operation identified by the identification unit 73 can be displayed in the operation type display field 313.

In the first embodiment, the second embodiment, and the third embodiment, the setting unit 74 enables or disables the recognition process that is performed by the recognition unit 72; however, the setting unit 74 can enable or disable giving of a notification of the result of the recognition process to thereby enable or disable the recognition unit 72. In this case, when disabling giving of a notification of the result of the recognition process, the setting unit 74 can, for example, stop output of the result of the recognition process to, for example, the image generation unit 71 while keeping the detection unit 76 and the determination unit 77 enabled to make the doctor or the like be unable to know the result of the recognition process. As a result, the setting unit 74 can enable or disable the recognition unit 72 more simply and quickly than in a case where the setting unit 74 enables or disables the recognition process itself.

Figure 13:
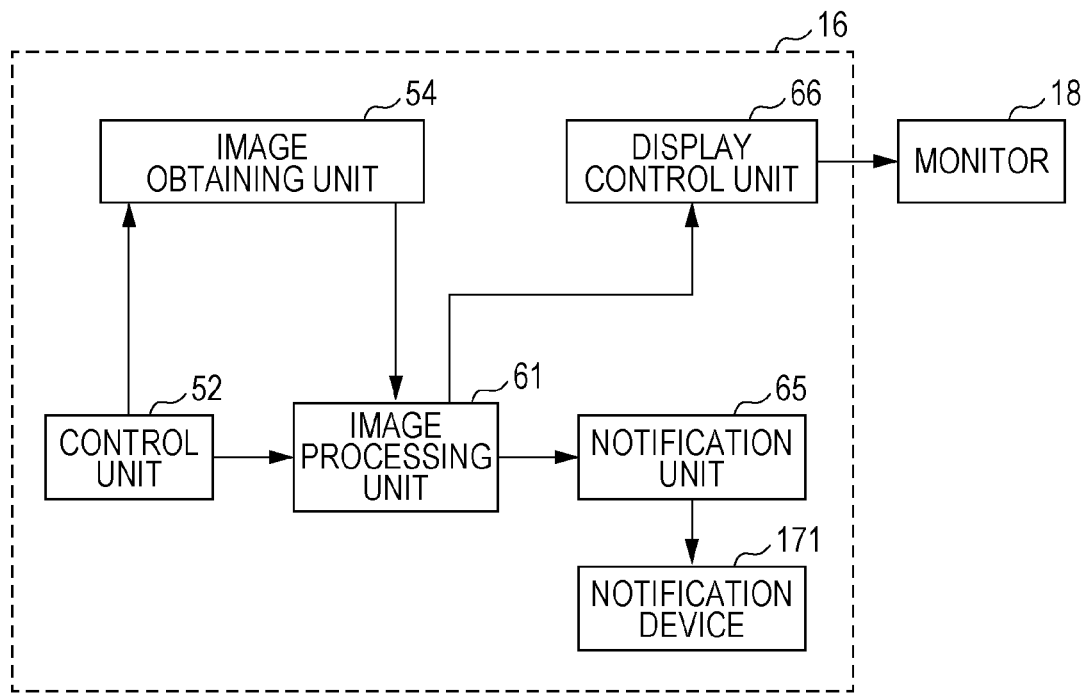
FIG. 13 is a block diagram of a processor device in a case where a notification of whether the recognition unit is enabled or disabled is given with a method other than display on a monitor.

In the first embodiment, the second embodiment, and the third embodiment, the notification unit 65 gives the notification of whether the recognition unit 72 is enabled or disabled by display on the screen of the monitor 18; however, in a case where the notification unit 65 gives the notification of whether the recognition unit 72 is enabled or disabled in a form other than display on the screen of the monitor 18, the processor device 16 can include a notification device 171 as illustrated in FIG. 13. The notification device 171 is, for example, a speaker that generates a sound or voice, an indicator formed of a light-emitting device, such as an LED, or a vibrating device, such as a motor or a piezoelectric element. In addition, the notification unit 65 can use, for example, a device included in the endoscope system 10 as the notification device 171. Further, the notification device 171 may be provided not in the processor device 16 but in the endoscope 12 or in the light source device 14.

Figure 14:
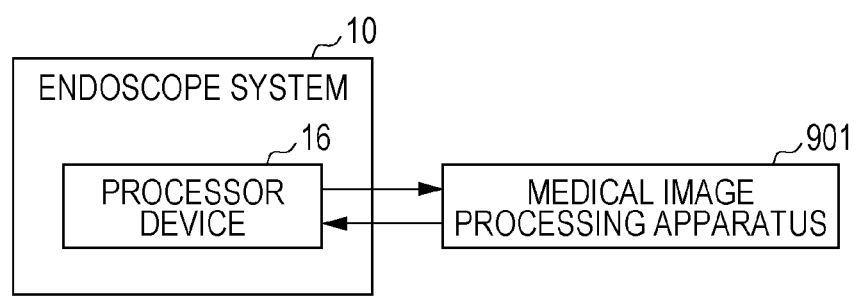
FIG. 14 is an explanatory diagram illustrating a medical image processing apparatus.
Figure 15:
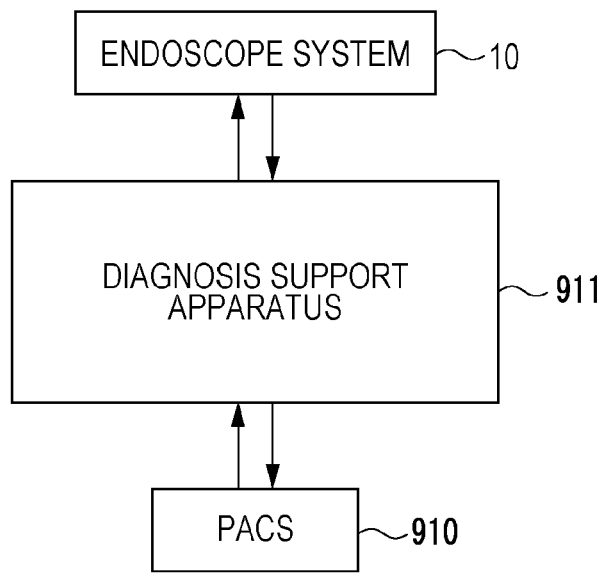
FIG. 15 is an explanatory diagram illustrating a diagnosis support apparatus.
Figure 16:
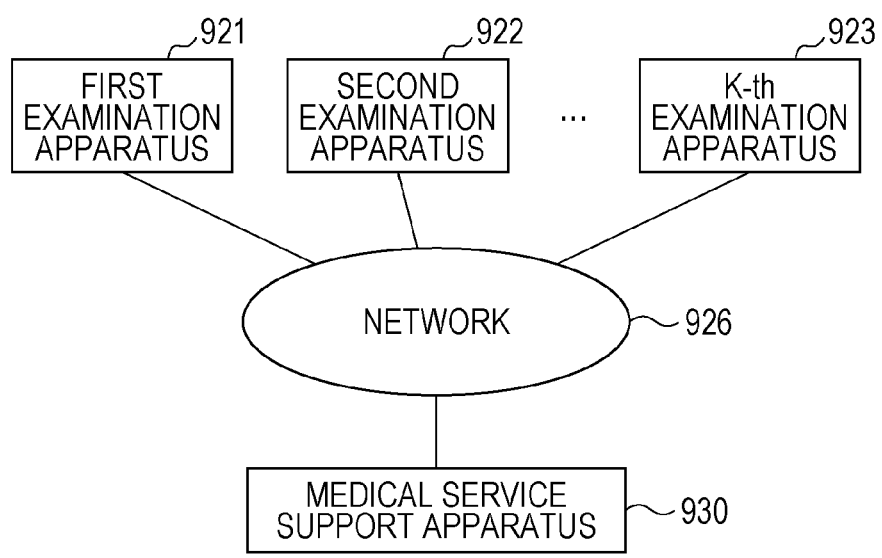
FIG. 16 is an explanatory diagram illustrating a medical service support apparatus.

As illustrated in FIG. 14, the recognition unit 72, the identification unit 73, the setting unit 74, and/or the notification unit 65 can be provided in, for example, a medical image processing apparatus 901 that communicates with the processor device 16 to cooperate with the endoscope system 10. As illustrated in FIG. 15, the recognition unit 72, the identification unit 73, the setting unit 74, and/or the notification unit 65 can be provided in, for example, a diagnosis support apparatus 911 that obtains directly from the endoscope system 10 (including one that does not have the notification unit 65 and so on) or indirectly from a PACS (Picture Archiving and Communication Systems) 910, raw images captured by the endoscope 12. Further, as illustrated in FIG. 16, the recognition unit 72, the identification unit 73, the setting unit 74, and/or the notification unit 65 can be provided in a medical service support apparatus 930 that is connected, via a network 926, to various examination apparatuses, such as a first examination apparatus 921, a second examination apparatus 922, . . . , a K-th examination apparatus 923, that include the endoscope system 10.

That is, the present invention includes a medical image processing apparatus including an image obtaining unit that obtains an image obtained by image capturing of a photographic subject, a recognition unit that performs a recognition process of recognizing the photographic subject by using the image, an identification unit that identifies an operation performed on the photographic subject, a setting unit that enables or disables the recognition unit in accordance with the result of identification by the identification unit, and a notification unit that gives a notification of whether the recognition unit is enabled or disabled, and an operation method for the medical image processing apparatus. Further, the present invention includes a diagnosis support apparatus including an image obtaining unit that obtains an image obtained by image capturing of a photographic subject, a recognition unit that performs a recognition process of recognizing the photographic subject by using the image, an identification unit that identifies an operation performed on the photographic subject, a setting unit that enables or disables the recognition unit in accordance with the result of identification by the identification unit, and a notification unit that gives a notification of whether the recognition unit is enabled or disabled, and an operation method for the diagnosis support apparatus. Similarly, the present invention includes a medical service support apparatus including an image obtaining unit that obtains an image obtained by image capturing of a photographic subject, a recognition unit that performs a recognition process of recognizing the photographic subject by using the image, an identification unit that identifies an operation performed on the photographic subject, a setting unit that enables or disables the recognition unit in accordance with the result of identification by the identification unit, and a notification unit that gives a notification of whether the recognition unit is enabled or disabled, and an operation method for the medical service support apparatus.

The present invention includes an operation method for an endoscope system, the operation method including a step of obtaining, by an image obtaining unit, an image obtained by image capturing of a photographic subject, a step of performing, by a recognition unit, a recognition process of recognizing the photographic subject by using the image, a step of identifying, by an identification unit, an operation performed on the photographic subject, a step of enabling or disabling, by a setting unit, the recognition unit in accordance with the result of identification by the identification unit, and a step of giving, by a notification unit, a notification of whether the recognition unit is enabled or disabled. Further, the present invention includes a processor device including an image obtaining unit that obtains an image obtained by image capturing of a photographic subject, a recognition unit that performs a recognition process of recognizing the photographic subject by using the image, an identification unit that identifies an operation performed on the photographic subject, a setting unit that enables or disables the recognition unit in accordance with the result of identification by the identification unit, and a notification unit that gives a notification of whether the recognition unit is enabled or disabled, and an operation method for the processor device.

Note that as the endoscope 12, a capsule endoscope can be used. In this case, the light source device 14 and part of the processor device 16 can be mounted in the capsule endoscope.

In the above embodiments, the hardware configuration of the processing units that perform various types of processing of, for example, the recognition unit 72, the identification unit 73, the setting unit 74, and the notification unit 65 is implemented as various processors as described below. The various processors include a CPU (central processing unit), which is a general-purpose processor executing software (program) to function as various processing units, a GPU (graphical processing unit), a programmable logic device (PLD), such as an FPGA (field-programmable gate array), which is a processor having a circuit configuration that is changeable after manufacture, and a dedicated electric circuit, which is a processor having a circuit configuration specifically designed to perform various types of processing.

One processing unit may be configured as one of the various processors or a combination of two or more processors of the same type or different types (for example, a plurality of FPGAs, a combination of a CPU and an FPGA, or a combination of a CPU and a GPU). Further, a plurality of processing units may be configured as one processor. As the first example of configuring a plurality of processing units as one processor, a form is possible where one or more CPUs and software are combined to configure one processor, and the processor functions as the plurality of processing units, a representative example of which is a computer, such as a client or a server. As the second example thereof, a form is possible where a processor is used in which the functions of the entire system including the plurality of processing units are implemented as one IC (integrated circuit) chip, a representative example of which is a system on chip (SoC). As described above, regarding the hardware configuration, the various processing units are configured by using one or more of the various processors described above.

Further, the hardware configuration of the various processors is more specifically an electric circuit (circuitry) in a form in which circuit elements, such as semiconductor elements, are combined.

Note that the present invention can be used in, for example, a system or an apparatus that obtains medical images (including moving images) other than endoscopic images as well as an endoscope system that, for example, obtains endoscopic images, a processor device, and other related apparatuses. For example, the present invention is applicable to ultrasonic examination apparatuses, X-ray imaging apparatuses (including CT (computed tomography) examination apparatuses and mammography apparatuses), and MRI (magnetic resonance imaging) apparatuses.

REFERENCE SIGNS LIST 10 endoscope system
12 endoscope
12a insertion part
12b operation part
12c bending part
12d tip part
12e angle knob
12f treatment tool insertion port
13a zoom operation part
13b water supply button
14 light source device
16 processor device
17 water supply tank
18 monitor
19 console
20 light source unit
22 light source control unit
30a illumination optical system
30b imaging optical system
45 illumination lens
46 object lens
47 zoom lens 48 image sensor
52 control unit
54 image obtaining unit
56 DSP
58 noise reduction unit
59 conversion unit
61 image processing unit
65 notification unit
66 display control unit
71 image generation unit
72 recognition unit
73 identification unit
74 setting unit
76 detection unit
77 determination unit
121, 126, 310, 321 endoscopic image
122, 127, 223, 224, 301 display
128 forceps
171 notification device
222 display field
311 coloring agent
313 type display field
331, 332, 333 icon
901 medical image processing apparatus
910 PACS
911 diagnosis support apparatus
921 first examination apparatus
922 second examination apparatus
923 K-th examination apparatus
926 network
930 medical service support apparatus
$S^{111}$ to $S^{118}$ operation steps

What is claimed is:

1. An endoscope system comprising:
one or more processors configured to:
obtain an image obtained by capturing a photographic subject;
perform a recognition process of recognizing the photographic subject by using the image, wherein the recognition process recognizes presence or absence of a lesion or a potential lesion of the photographic subject or recognizes a type or a degree of progression of a lesion or a potential lesion of the photographic subject;
identify an operation performed on the photographic subject;
enable or disable the recognition process in accordance with a result of identifying the operation performed on the photographic subject;
provide a notification for indicating a state of the recognition process;
in a case where the notification indicates that the state of the recognition process is an enabled state, display information indicating the state of the recognition process, and further display either information indicating a detection position of the lesion or the potential lesion or information indicating the type or the degree of progression of the lesion or the potential lesion, on a display; and
in a case where the notification indicates that the state of the recognition process is a disabled state, display information indicating the state of the recognition process, on the display,
wherein the information indicating the state of the recognition process comprises a character string, a letter, a geometric shape, and or a symbol representing the state of the recognition process.

2. The endoscope system according to claim 1, wherein the one or more processors determine whether or not an operation is performed on the photographic subject.

3. The endoscope system according to claim 2, wherein the one or more processors disable the recognition unit in a case where an operation is performed on the photographic subject, and enable the recognition process in a case where no operation is performed on the photographic subject.

4. The endoscope system according to claim 1, wherein the one or more processors identify a type of the operation performed on the photographic subject.

5. The endoscope system according to claim 4, wherein the one or more processors disable the recognition process in a case where a specific operation is performed on the photographic subject.

6. The endoscope system according to claim 1, wherein the operation identified by the one or more processors is use of a treatment tool.

7. The endoscope system according to claim 1, wherein the operation identified by the one or more processors is spraying of a liquid on the photographic subject.

8. The endoscope system according to claim 1, wherein the one or more processors enable or disable giving of a notification of a result of the recognition process.

9. The endoscope system according to claim 1, wherein the one or more processors give a notification of the result of identification of the operation performed on the photographic subject in addition to the notification for indicating the state of the recognition process.

10. The endoscope system according to claim 1, wherein in a case where the one or more processors perform a plurality of types of recognition processes, the one or more processors enable or disable each of the recognition processes.

11. The endoscope system according to claim 1, wherein the operation is an operation that decreases accuracy of the recognition process.

12. The endoscope system according to claim 1, wherein the operation includes removal of tissue from a living body, treatments related to surgical resection or resection treatment, spraying of a liquid on the photographic subject, or cleaning of the photographic subject.

13. The endoscope system according to claim 1, wherein the notification is a notification of whether the recognition process by use of an artificial intelligence is enabled or disabled.

14. The endoscope system according to claim 1, wherein the operation identified by the one or more processors is an operation that changes a color of the photographic subject by a user.

15. The endoscope system according to claim 1, wherein the operation is an operation performed with respect to the photographic subject.

16. The endoscope system according to claim 1, wherein the operation identified by the one or more processors is spraying of a coloring agent or a fluorescent drug on the photographic subject.

17. The endoscope system according to claim 1, wherein the recognition process further obtains or calculates biological function information about the photographic subject in part or in whole, and
wherein recognition of the type of the lesion or the potential lesion is, in a case where the lesion or the potential lesion is a polyp, to determine the type as adenoma, hypertrophic polyp, or cancer.

18. The endoscope system according to claim 17, wherein recognition of the degree of progression of the lesion or the potential lesion is, in a case where the lesion or the potential lesion is the cancer, to determine a stage of the cancer, or to determine a narrow-band imaging international colorectal endoscopic classification or a Japan narrow-band imaging expert team classification.

19. A recognition method of an endoscope system comprising-a processor, the recognition method comprising:
   obtaining an image obtained by capturing a photographic subject;
   performing a recognition process of recognizing the photographic subject by using the image, wherein the recognition process recognizes presence or absence of a lesion or a potential lesion of the photographic subject or recognizes a type or a degree of progression of a lesion or a potential lesion of the photographic subject;
   identifying an operation performed on the photographic subject;
   enabling or disabling the recognition process in accordance with a result of identifying the operation performed on the photographic subject;
   providing a notification for indicating a state of the recognition process;
   in a case where the notification indicates that the state of the recognition process is an enabled state, displaying information indicating the state of the recognition process, and further displaying either information indicating a detection position of the lesion or the potential lesion or information indicating the type or the degree of progression of the lesion or the potential lesion, on a display; and
   in a case where the notification indicates that the state of the recognition process is a disabled state, displaying information indicating the state of the recognition process, on the display,
   wherein the information indicating the state of the recognition process comprises a character string, a letter, a geometric shape, and or a symbol representing the state of the recognition process.

* * * * *